United States Patent [19]

Reeves

[11] Patent Number: 4,981,042

[45] Date of Patent: Jan. 1, 1991

[54] APPARATUS FOR DETERMINING THE DENSITY OF A LIQUID

[76] Inventor: Goodwyn G. Reeves, P.O. Box 37147, Raleigh, N.C. 27627

[21] Appl. No.: 252,748

[22] Filed: Oct. 3, 1988

[51] Int. Cl.$^5$ .............................................. G01N 9/16
[52] U.S. Cl. ...................................................... 73/454
[58] Field of Search ................ 73/451, 452, 453, 454, 73/434, 445; 250/231 R, 237 G

[56] References Cited

U.S. PATENT DOCUMENTS

| | | | |
|---|---|---|---|
| 1,257,662 | 2/1918 | Young | 73/451 |
| 2,460,503 | 2/1949 | Howe | 73/453 |
| 2,530,981 | 11/1950 | Mikina | 73/452 |
| 3,363,148 | 1/1968 | Freeman | 250/231 R |
| 3,766,786 | 10/1973 | Gehatia et al. | 673/453 |
| 3,782,199 | 1/1974 | Bell | 73/452 |

Primary Examiner—John Chapman
Attorney, Agent, or Firm—Rhodes, Coats & Bennett

[57] ABSTRACT

An instrument for measuring the density of a liquid is disclosed comprising a housing having a solution chamber, and a separate instrument chamber. The solution and instrument chambers are separated by an isolating means, a portion of which is flexible. A lever passes through the flexible portion of the isolating means and is supported by a pivot assembly. A float is attached to one end of the lever and is at least partially submerged in the liquid being measured. Variations in the density of the liquid causes the float to rise and fall, and consequently, the lever rotates about the pivot axis. Position sensing electronics contained within the instrument chamber sense the position of the lever which is indicative of the liquid density. The isolating means includes an isolating partition having an opening formed therein, and a diaphragm. The diaphragm is clamped to a raised collar surrounding the opening in the isolating partition by a clamping ring. The clamping ring includes two integrally formed and diametrically opposed pivot blocks having pivot holes formed therein. The pivot assembly is mounted to the pivot blocks by pivot pins which lie within the plane of the diaphragm. This arrangement minimizes the deformation of the diaphragm caused by rotation of the lever, and also minimizes the effect of the force exerted by the diaphragm on the lever.

16 Claims, 2 Drawing Sheets

APPARATUS FOR DETERMINING THE DENSITY OF A LIQUID

FIELD OF THE INVENTION

The present invention relates generally to apparatuses for determining the density of a liquid and more particularly to an isolating means therefor for separating sensitive components from the liquid being measured.

BACKGROUND OF THE INVENTION

Solution mass density can be used to monitor the condition of a chemical solution which changes as it is used in a process. In some instances, the density of the solution should be maintained within fairly precise limits. For example, in the case of ammoniacal etchant solutions for copper, it is desirable to maintain etchant density to within 0.1% of a set value. An alarm should be provided to warn the operator that the process is out of control if the density varies more than 0.25% from the set value.

A hydrometer float is commonly used to provide a simple, stable indicator of mass density. Variation in the float height changes with the density of the liquid displaced by the float. The float height variation can be monitored electronically and used to generate control signals for automatically replenishing the solution and/or alarm signals.

In many instances, the solution being measured is corrosive, and contains entrained or dissolved gases. The solution can roughen and opacify common plastic materials by attack and deposition. Instruments which rely upon mechanical movement of the hydrometer float along a vertical guide or about a pivot may be prone to error due to increasing friction as deposits accumulate on the guides or pivots. Also, the electronics which sense the position of the float must be isolated from the corrosive solution and fumes. The isolating means may introduce unacceptable errors if it imposes excessive uncontrolled forces on the float, the vertical guides, or pivot.

SUMMARY OF THE INVENTION

The present invention is an instrument for determining the density of a solution. The instrument comprises a housing having first and second chambers divided by an isolating partition. An opening is formed in the isolating partition and surrounded by a raised collar. A flexible diaphragm is secured about its perimeter to the raised collar to isolate the instrument chamber from corrosive fumes emitted from the solution being tested.

The instrument includes a lever supported by a pivot assembly disposed within the instrument chamber. The hydrometer float is attached to the lever and is at least partially submerged in the solution. Variations in the density of the solution will cause the float to rise and fall, and consequently, the lever will rotate about its pivot. Position sensing electronics are contained within the instrument chamber and are actuated by the lever to sense the change in position of the lever which is indicative of the mass solution density. The position sensing electronics generates output signals which may be utilized to automatically adjust the mass solution density or to provide an alarm warning the process supervisor.

The positioning of the lever pivot and sensor elements within a separate chamber isolated from the solution minimizes error resulting from the corrosive effects of the solution being measured. Additionally, the pivot lies in the same plane as the diaphragm minimizing the effect of the diaphragm's restoring torque on the lever. Thus, a simple and accurate device is provided for measuring density of the solution.

Accordingly, it is the primary object of the present invention to provide an apparatus for measuring mass solution density that minimizes the effect of friction and other external forces unrelated to the density of the solution being measured.

Another object of the present invention is to provide an apparatus for measuring mass solution density in which sensitive electronic components are isolated from the corrosive effects of the solution being measured and the gases entrained or dissolved therein.

Another object of the present invention is to provide a reliable and stable indicator of mass solution density that minimizes error resulting from friction and the corrosive effects of the solution being measured.

Other objects and advantages of the present invention will become apparent and obvious from a study of the following description and the accompanying drawings which are merely illustrative of such invention.

DESCRIPTION OF THE INVENTION

Figure 1:
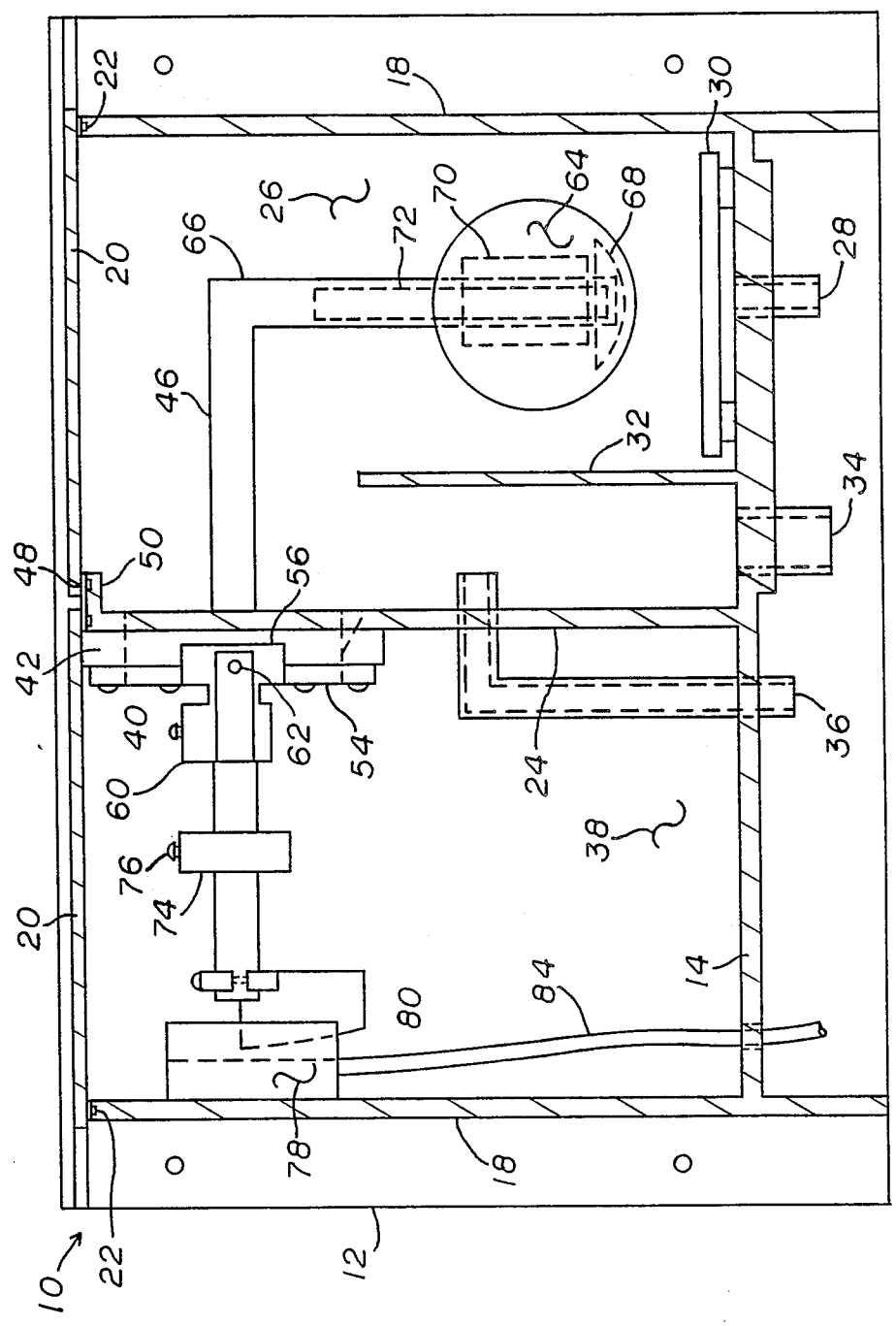
FIG. 1 is a side sectional view of the measuring device.
Figure 2:
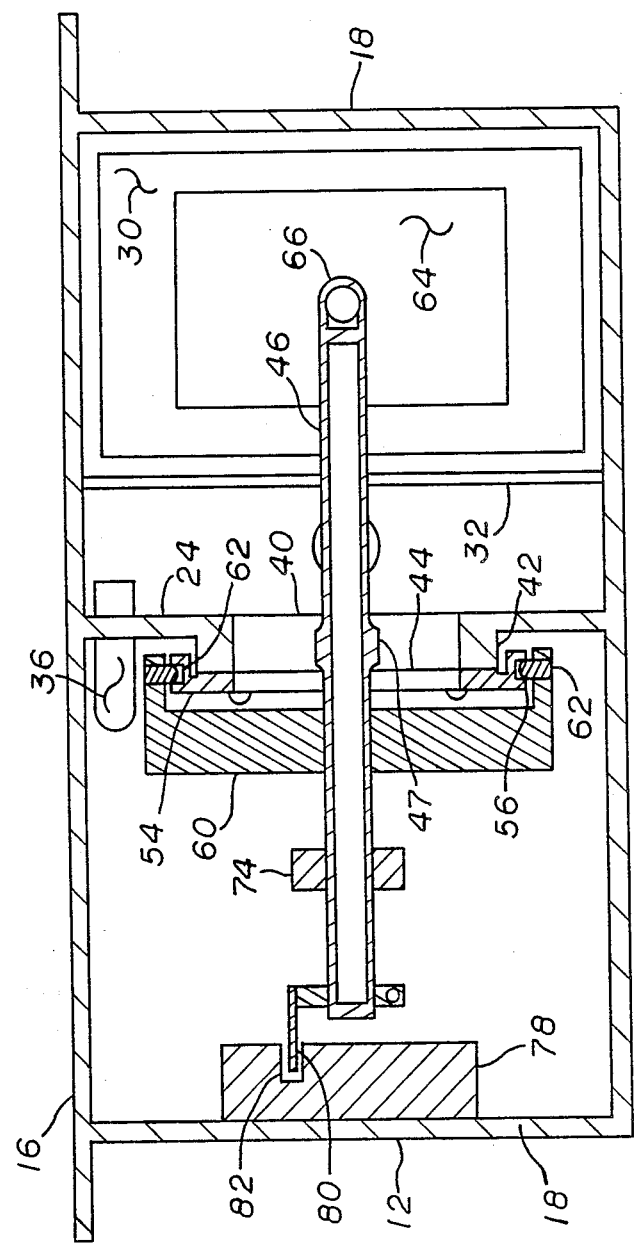
FIG. 2 is a top sectional view of the measuring device.

Referring now to the drawings, the measuring device of the present invention is shown and indicated generally by the numeral 10. The measuring device 10 includes a housing 12 made of a material such as rigid polyvinylchloride (PVC) or high density polyethylene which has adequate strength and will withstand the corrosive effects of the solution to be measured. The housing includes a bottom 14, side walls 16, and end walls 18. Top panels 20 provide a removable closure to permit access to the internal components of the hydrometer.

An isolating partition 24 divides the housing 12 into two distinct chambers referred to herein as the solution chamber 26 and instrument chamber 38. A continuous supply of solution enters the solution chamber 26 through inlet 28 from a pressurized source. The solution is distributed over the bottom of the solution chamber 26 by a baffle plate 30. The solution rises within the solution chamber 26 until it reaches the top of the dam 32. The solution spilling over the top edge of the dam 32 exits the housing 12 through drain 34 and returns to the processing machine utilizing the solution. A vent pipe 36 maintains atmospheric pressure within the solution chamber 26 and provides means for gases released from the solution to escape to the atmosphere. If the produced gases are hazardous, the inlet of a mechanical ventilation system (not shown) can be placed adjacent to the outlet of the vent pipe 36 to pull fumes into the mechanical ventilation system. Direct connection to the vent pipe should be avoided since a pressure differential between the chambers 26 and 38 may introduce error into the readings.

The isolating partition 24 separating the solution chamber 26 from the instrument chamber 38 includes an opening 40 surrounded by a raised collar 42 that extends into the instrument chamber 38. A lever 46 extends through the opening 40 in the isolating partition 24. A flexible diaphragm 44 seals space between the lever 46 and the border of the opening. The diaphragm 44 includes an outer periphery that is clamped to the raised collar 42 by means of a clamping ring 54 and an inner periphery that is secured to a boss 47 formed on the intermediate portion of the lever 46. The diaphragm 44 prevents vapors and liquid droplets contained within the solution chamber 26 from entering into the instrument chamber 38. Escape of the vapors into the atmosphere is prevented by gaskets 22 inserted into grooves formed top edges of sidewalls and endwalls and by gaskets 48 in the flange 50 at the top of the isolating partition 24.

The lever 46 is supported by a pivot assembly disposed within the instrument chamber 38. The pivot assembly includes the clamping ring 54 which has two diametrically opposed pivot blocks 56. The lever 46 is attached to and supported by a yoke 60. The yoke 60 is secured to pivot blocks 56 which form an integral part of the clamping ring 54, by a pair of pivot pins 62. The pivot pins 62 are fixed to and extend from the yoke 60 into smooth-walled holes 58 in the pivot blocks 56. The ends of the pivot pins 62 are preferably rounded and touch the flat smooth bottoms of the holes 58 to provide accurate lateral positioning of the lever 46 within the opening 40.

A hydrometer float 64 is attached to one end of the lever 46 by means of a hollow float pipe 66. The bottom of the float is rounded to prevent the accumulation of gas bubbles which could adhere to a flat bottom and significantly increase the buoyant force on the float 64.

The float 64 contains three ballast weights. Ballast weight 68 is disposed in the bottom of the float 64. Ballast weight 70 surrounds the float pipe 66, and ballast weight 72 extends into the float pipe 66. The ballast weights 68, 70 and 72 are selected by the manufacturer and sealed in the float 64 during assembly. The ballast weights together with the counterweight 74 determines the position at which the lever 46 will be horizontal. The counterweight 74 is mounted on the lever 46 and secured by a set screw 76. The counterweight 74 can be moved along the lever 46 to adjust the liquid density value at which the lever 46 will be on a horizontal position. Changes in the density of the solution will of course cause the float 64 to rise or fall, as the case may be, resulting in rotation of the lever 46.

The sensitivity of the instrument to changes in density can be adjusted by selectively positioning the center of mass of the lever 46 and attached components with respect to a reference line extending from the center of the pivot to the center of floatation. Raising the center of mass above this line increases the sensitivity of the float. That is, positioning the center of mass above the reference line will result in a greater change in float height per unit change in density. Positioning the center of mass below the reference line has the opposite effect. It is preferred when practicing the invention, that the center of mass be as close as possible to the reference line.

A position sensor 78 is mounted within the instrument chamber 38 to sense the position of the lever 46. The position sensor 78 can be utilized to determine whether the solution density is above or below the desired controlled value, whether the solution density has exceeded upper and/or lower limits requiring alarm activation, and can if desired determine and report the solution density value. A simple way to frictionlessly sense lever position is to attach an optically opaque card 80 to lever 46 at the end of opposite float 64. The card 80 passes through a slot 82 in the position sensor's housing. The card 80 interrupts one or more light beams projecting across the slot 82 to provide an indication of lever positioning. Alternatively the card 80 can be coded with an array of transparent and opaque areas to allow reporting of lever positions and/or corresponding solution density as a digital numeric value. Lever position information is carried by cable 84 to a control system (not shown) which provides visual and/or audible signals to the process supervisor and automatically controls readjustment of solution density. If desired, a pointer can be attached to the lever 46 and a visible scale can be mounted in housing 12 to provide a direct mechanical indication of solution density.

In operation, a continuous supply of solution enters the solution chamber 26 through inlet 28. The level of the solution remains constant since the excess solution flows over the top of the dam 32 and exits the drain 34. The float 64 rises to the level at which the sum of the moments about pivot pins 62 from the buoyant force exerted on the float 64 and float pipe 66 and the weight of the lever arm 46 and attached components equal zero. If the weights 68 through 72 are properly chosen and the counter weight 74 properly positioned, the lever 46 will be horizontal and the diaphragm 44 nondistorted when the solution density is near its desired control value. If the solution density increases, the volume of solution displaced by the float 64 and float pipe 66 will decrease causing the float to rise. The float rise tilts the lever 46 causing the card 80 to drop in slot 82 where the change in the position of the lever 46 is detected. A decrease in solution density will result in increased displacement of solution by float 64 and float pipe 66 causing the float 64 to sink.

The movement of the lever 46 deforms the diaphragm 44. The deformation of the diaphragm 44 when the lever 46 rotates produces a force which tends to rotate the lever towards the level position. The present invention minimizes the effect of the restoring diaphragm forces on the lever by locating the pivot pins 62 in the plane of the diaphragm 44. This arrangement minimizes diaphragm deformation as the lever 46 rotates resulting in smaller diaphragm forces. Additionally, this arrangement makes the effective moment arm of the diaphragm forces negligible when compared to the moment arm of the buoyant forces acting on the hydrometer float 64 and float pipe 66. It is appreciated that nonplanar diaphragms may also be used to practice the present invention. In such a case, the pivot axis should be at a point adjacent to the diaphragm and most preferably at the point where forces exerted by diaphragm on the lever are minimized.

Friction errors due to the pivot are also kept small by protecting the pivot assembly from corrosion and deposits by locating them on the protected side of the isolating partition 24. The electronics are similarly protected from attack by the corrosive liquid and fumes. Therefore, a simple and reliable indicator of solution mass density is provided.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An apparatus for measuring density of a liquid comprising:
   (a) a housing including an isolating means having a flexible member for defining a solution chamber on one side of the isolating means and an instrument chamber on the opposite side of the isolating means;
   (b) a lever disposed within the housing and extending through the flexible member of the isolating means;
   (c) a pivot assembly for rotatably supporting the lever independently of the flexible member of the isolating means, the axis of rotation of the pivot assembly being positioned along the lever at a point where the lever passes through the flexible member so as to reduce the effect of the forces exerted by the flexible member on the lever;
   (d) a float disposed within the solution chamber and at least partially submerged in the solution, the float being secured to the lever so that variations in the density of the liquid causes changes in the float height which rotates the lever about the pivot axis; and
   (e) position sensor means mounted within the instrument chamber for sensing the rotational position of the lever as the lever rotates about the pivot axis, the position being indicative of the specific gravity of the solution.

2. The apparatus according to claim 1 wherein the isolating means comprises an isolating partition having an opening formed therein, and the flexible member seals the opening in the isolating partition.

3. The apparatus according to claim 2 wherein the pivot assembly is mounted in the instrument chamber.

4. The apparatus according to claim 2 wherein the flexible member is a generally planar diaphragm which flexes when the lever rotates from its normal horizontal position.

5. The apparatus for measuring density of a liquid according to claim 5 wherein the lever includes a boss, and wherein the diaphragm includes an inner periphery secured to the boss and an outer periphery secured to the border of the opening in the isolating partition.

6. The apparatus according to claim 4 wherein the pivot axis of the lever lies substantially in the plane of the diaphragm to minimize the force exerted by the diaphragm on the lever.

7. The apparatus according to claim 6 wherein the pivot assembly is mounted in the instrument chamber.

8. The apparatus for measuring density of a liquid according to claim 7 wherein the pivot assembly includes a clamping ring for securing the outer periphery of the diaphragm;

9. The apparatus for measuring density of a liquid according to claim 8 wherein said clamping ring includes two diametrically opposed pivot blocks having pivot holes formed therein, and wherein said pivot assembly includes a yoke having a pair of pivot pins aligned along the pivot axis and extending from the yoke into respective pivot holes.

10. The apparatus for measuring density of a liquid according to claim 1 further including balancing means for adjusting the liquid density value at which the lever will be in a horizontal position.

11. The apparatus for measuring the density of a liquid according to claim 1 wherein the position sensing means comprises an optical sensor of the type producing at least one beam of light, and a card mounted to the lever, a portion of which is opaque so as to interrupt the beam of light as the lever rotates about its pivot axis.

12. The apparatus according to claim 1 wherein the pivot assembly includes a pin on which the lever rotates.

13. An apparatus for measuring the density of a liquid comprising:
   (a) a housing;
   (b) an isolating partition dividing the housing into a solution chamber adapted to receive the liquid being measured and an instrument chamber, the isolating partition having an opening formed therein and a mounting collar surrounding the opening and projecting into the instrument chamber;
   (c) a flexible, liquid impervious, planar diaphragm for sealing the opening in the isolating partition including an outer periphery secured to the mounting collar;
   (d) a lever disposed within the housing and extending through the diaphragm;
   (e) a float assembly mounted within the housing including:
      (1) a pivot assembly mounted within the instrument chamber of the housing for supporting the lever independently of the diaphragm, said pivot assembly having a pivot axis that lies in the plane of the diaphragm;
      (2) a float connected to the lever and at least partially submerged in the liquid, wherein variations in the density of the liquid will cause changes in the height of the float and consequently cause the lever to rotate about the pivot axis with changes in density of the liquid; and
   (e) position sensing means disposed with the instrument chamber for determining the rotational position of the lever which is indicative of the liquid density.

14. The apparatus according to claim 13 wherein the pivot assembly includes a clamping ring for securing the outer periphery of the diaphragm to the mounting collar, the clamping ring including two diametrically opposed pivot blocks having pivot holes formed therein; and a yoke having a pair of pivot pins extending therefrom into respective pivot holes in the pivot block.

15. The apparatus for measuring the density of a liquid according to claim 13 further including a counterweight movable along the lever to allow the operator to adjust the liquid density value at which the lever will be in a horizontal position.

16. The apparatus for measuring the density of a liquid according to claim 13 wherein said position sensing means comprises an optical sensor of the type producing at least one beam of light, and a card mounted to the lever, a portion of which is opaque so as to interrupt the beam of light as the lever rotates about its pivot axis.

* * * * *

UNITED STATES PATENT AND TRADEMARK OFFICE
CERTIFICATE OF CORRECTION

PATENT NO. : 4,981,042

DATED : January 1, 1991

INVENTOR(S) : Goodwyn G. Reeves

It is certified that error appears in the above-identified patent and that said Letters Patent is hereby corrected as shown below:

On the title page, item [76] Inventor: please change the inventor's address to read --Post Office Box 37157--.

Column 3, line 40, delete "position" and substitute --solution density--.

Signed and Sealed this

Fourteenth Day of July, 1992

Attest:

DOUGLAS B. COMER

*Attesting Officer*  *Acting Commissioner of Patents and Trademarks*